United States Patent [19]

Yoshikawa et al.

[11] Patent Number: 4,824,780

[45] Date of Patent: Apr. 25, 1989

[54] METHOD FOR PRODUCING HYDROQUINONE

[75] Inventors: Akira Yoshikawa; Hiroko Sato, both of Niigata, Japan

[73] Assignee: Director-General of Agency of Industrial Science and Technology, Tokyo, Japan

[21] Appl. No.: 703,307

[22] Filed: Feb. 20, 1985

[30] Foreign Application Priority Data

Apr. 3, 1984 [JP] Japan .................................. 59-65154
Apr. 3, 1984 [JP] Japan .................................. 59-65155

[51] Int. Cl.$^4$ ........................... C12P 7/66; C12R 1/32
[52] U.S. Cl. ..................................... 435/133; 435/863
[58] Field of Search ............... 435/133, 132, 136, 155, 435/156, 157, 253, 863

[56] References Cited

U.S. PATENT DOCUMENTS 4,455,373  6/1984  Higgins .............................. 435/132

FOREIGN PATENT DOCUMENTS 0073134  3/1983  European Pat. Off. .
0098138  1/1984  European Pat. Off. .
2024205A 1/1980  United Kingdom .

OTHER PUBLICATIONS

Yoshikawa et al., "Hydroquinone", *Chemical Abstracts*, vol. 104, No. 1, p. 429 (Jan. 1986) Abst. No. 4663g.
"A Kinetic Study of Benzene Oxidation to Phenol by Hyman, et al., Whole Cells of Nitrosomonas European and Evidence for Further Oxidation of Phenol to Hydroquinone", *Chemical Abstracts*, vol. 104, No. 9, p. 394 (Mar. 1986), Abst. No. 65594g.
Biochemical and Biophysical Research Communications vol. 89, No. 2, 1979, pp. 671–677.
European Search Report 85301262, 1987 (Feb.).

*Primary Examiner*—Thomas G. Wiseman
*Assistant Examiner*—Thomas D. Mays
*Attorney, Agent, or Firm*—Ladas & Parry

[57] ABSTRACT

Hydroquinone is isolated from the reaction medium resulting from contacting cultured Mycobacterium cells containing an oxygenase with benzene and/or phenol in the presence of molecular oxygen or air and aqueous medium.

3 Claims, No Drawings

METHOD FOR PRODUCING HYDROQUINONE

BACKGROUND OF THE INVENTION

This invention relates to a process for producing hydroquinone and more particularly, it relates to a process for producing hydroquinone by biochemical oxidation of benzene and/or phenol.

Hydroquinone is an industrially important compound which is widely used as photographic developers, antioxidants and synthetic intermediates.

At present, hydroquinone is mainly prepared by chemical synthesizing methods, which have defects such as complexity of process, by-production of catechol in large amounts which causes increase in load at the subsequent removal step and difficulty in balancing of supply and demand of both the compounds.

Thus, a process for producing hydroquinone which is free of these defects has been demanded.

Generally, biochemical oxidation has a high selectivity and yields substantially no by-products and has advantages on these points.

This is also applicable to production of hydroquinone and there have been processes for production of hydroquinone with microorganisms, for example, in Japanese Patent Laid-Open Applications (Kokai) No. 157895/79, No. 47496/83 and No. 65187/82. However, in these processes only two microorganisms, *Methylosinus trichosporium* and *Methylococcus capsulatus* which are methane-assimilating bacteria are used.

After the inventors' intensive researches on biochemical oxidation, it has been found that some of microorganisms belonging to either of Rhodococcus or Mycobacterium have ability to oxidize benzene or phenol to product hydroquinone. The inventors have established a process for production of hydroquinone with use of benzene or phenol as a starting material and of said microorganisms. This process is simple and produced hydroquinone in high yield without by-products, because the reaction proceeds position-specifically.

SUMMARY OF THE INVENTION

This invention resides in a process for producing hydroquinone which comprises contacting cells defined below and/or after-treatment products thereof containing an oxygenase system, which may be called merely "cell after-treatment products", hereinafter, with benzene and/or phenol in the presence of molecular oxygen or air and an aqueous medium and in the presence or absence of an electron source, said cells being obtained by culturing a microorganism belonging to Rhodococcus or Mycobacterium and capable of oxidizing benzene and/or phenol.

DESCRIPTION OF THE INVENTION

These microorganisms used in this invention may be those which belong to Rhodococcus or Mycobacterium and are capable of oxidizing benzene and/or phenol. Representatives of microorganisms belonging to Rhodococcus are *Rhodococcus rhodochrous*, etc. These are known and available from collections such as ATCC (American Type Culture Collection) and the like.

Rhodococcus and *Rhodococcus rhodochrous* are disclosed in "Journal of General Microbiology 100 99–122 1977".

As representatives of microorganisms belonging to Mycobacterium, mention may be made of *Mycobacterium vaccae, Mycobacterium album*, etc. These are known and may be available from collections such as ATCC. Mycobacterium is disclosed in Bergey's Manual of Determinative Bacteriology 8th eddition, *Mycobacterium vaccae* is disclosed in "Int. J. Syst. Bact. 30, 328, 1980" and *Mycobacterium album* is disclosed in "Zentrabl Bakteriol Parasiten Infektionskr Hyg Abt II 37, 595609, 1913".

The methane-assimilating bacteria *Methylosinus trichosporium* and *Methylococcus capsulatus* can utilize only methane or methanol as a carbon source while microorganisms belonging to Rhodococcus or Mycobacterium can utilize various compounds as carbon sources and have advantages in this respect.

As the carbon sources in a culturing medium for culturing these microorganisms belonging to Rhodococcus or Mycobacterium to obtain cells used for reactions to produce hydroquinone, mention may be made of, for example, alkanes such as propane, n-butane, etc., alcohols such as n-butanol, etc., organic acids such as n-butyric acid, etc., sugars such as glucose, etc. Any of these substrates may be used for culturing the microorganisms. Of these substrates especially preferred are alkanes such as propane and n-butane which have 2 or more carbon atoms and are gaseous at the normal condition.

As nitrogen sources in the culturing medium, mention may be made of ammonium sulfate, ammonium chloride, etc. In addition thereto, inorganic salts which are usually used for culturing bacteria may also be added to the culturing medium.

Culturing temperature is preferably 25° to 35° C. and culturing pH is preferably about 7.

After culturing, cells can be obtained by ordinary solid-liquid separating means such as centrifugal separation, filtration, etc.

The reaction may be carried out by suspending the cells, as they are, in a buffer solution and the like. Instead, the cells may be used in the immobilized form on a carrier. Alternatively, enzyme which is obtained by crushing the cells by ultrasonic treatment, etc., may be used as it is, or in the immobilized form.

Reaction conditions may be such that the oxidizing ability of the cells or of the after-treatment product thereof is not lost. For example, reaction temperature of 25° to 35° C. and pH of about 7 are preferred like the culturing conditions. Oxygen is required besides benzene and/or phenol as substrates for the reaction. The oxygen is dissolved in reaction liquid. Shaking a reactor, for example, is preferred in order to promote the dissolution of oxygen.

The aqueous medium used for the reaction includes water, a culturing medium and an aqueous solution of inorganic compounds. As the aqueous solution of inorganic compounds, for example, various buffer solutions may advantageously be used.

When the reaction is carried out batch-wise, an amount of benzene or phenol to be added to 1 liter of reaction liquid is preferably 0.5 to 1 g and the cell concentration is preferably 0.5 to 40 g/liter.

When reaction rate is made large or the cell is repeatedly used for reaction, culturing is effected preferably in a culturing medium containing excess electron source. Alternatively, the electron source is previously brought into contact with the cell used for reaction or is allowed to be present in the reaction system. As the electron source, mention may be made of n-butanol, 2-butanol, n-butyric acid, glucose, etc. and glucose is especially preferred. Concentration of the electron source in the reaction liquid is generally 0.1 to 2 g per liter of the reaction liquid.

Progress of the reaction can be monitored by examining the concentration of substrate remaining in the reaction supernatant liquid by gas chromatography or high performance liquid chromatography.

After completion of the reaction, reaction product liquid is separated from such solid matters as cells by means of ordinary solid-liquid separating means such as centrifugal separation until a supernatant liquid containing hydroquinone is obtained. The cells separated and recovered can be repeatedly used for the reaction.

Separation and recovery of hydroquinone from the supernatant liquid may be carried out, for example, by extraction and transfer with organic solvents and subsequent evaporation to dryness. Preferred organic solvents are methyl isobutyl ketone, ethyl acetate, etc.

Thus, according to this invention, hydroquinone can be easily and efficiently obtained.

This invention is further illustrated by the following examples.

EXAMPLE 1

*Rhodococcus rhodochrous* ATCC 21197 was cultured in a complete synthetic culture medium (pH 7.0) containing n-butane as a carbon source at 30° C. for 48 hours. Then n-butane was supplied to a space in the reactor as a mixed gas with air (n-butane:air=1:3). After culturing, the cells were obtained by centrifugal separation.

Thereafter, these cells were suspended in a phosphate buffer solution (pH 7.0) containing $Mg^{++}$ and previously heated to 30° C. Concentration of cells was 3 mg/ml. To 20 ml of this suspension was added 500 mg/liter of phenol and reaction was effected at 30° C. for 24 hours with shaking to produce 80 mg/liter of hydroquinone in supernatant liquid. No by-products were detected.

EXAMPLE 2

In the same manner as in Example 1, *Rhodococcus rhodochrous* ATCC 21197 was cultured in a complete synthetic culture medium (pH 7.0) containing n-butane as a carbon source at 30° C. for 48 hours. After culturing, cells were obtained by centrifugal separation.

These cells were suspended in a phosphate buffer solution (pH 7.0) containing $Mg^{++}$ previously heated to 30° C. Concentration of cells was 3 mg/ml. To 20 ml of this suspension were added phenol and glucose in amounts of 500 mg/liter and 300 mg/liter, respectively. Reaction was carried out at 30° C. for 15 hours with shaking. As a result, 85 mg/litre for hydroquinone was produced in supernatant liquid. No by-products were detected.

EXAMPLE 3

*Rhodococcus rhodochrous* ATCC 21197 was cultured in the same manner as in Example 1 except that a complete synthetic culture medium (pH 7.2) containing glucose (1 weight% added) as a carbon source was used and culturing was effected for 24 hours.

Thus obtained cells were suspended in a phosphate buffer solution (pH 7.0) containing $Mg^{++}$ previously heated to 30° C. to obtain a suspension of cells. Concentration of cells was 10 mg/ml. To 20 ml of this suspension was added 12 μl of benzene in a conical flask of 100 ml which was the reactor. The reactor was closed and reaction was carried out at 30° C. for 24 hours with shaking. As a result, 5 mg/liter of hydroquinone was produced.

EXAMPLE 4

*Mycobacterium vaccae* ATCC 29678 was cultured in a complete synthetic culture medium (pH 7.0) containing n-butane as a carbon source at 30° C. for 72 hours. The n-butane was supplied to space in the reactor as a mixed gas with air (n-butane:air=1:3). After culturing, cells were obtained by centrifugal separation. These cells were suspended in 500 ml of a phosphate buffer solution (pH 7.0) containing $Mg^{++}$ previously heated to 30° C. Concentration of cells was 10 mg/ml. 500 ml of this suspension was poured into a conical flask of 5 liter previously sterilized, followed by adding 250 mg of benzene and 250 mg of glucose. Then, the flask was closed with a silicone rubber cock. Reaction was carried out using a shaking culture device at 30° C. for 15 hours. After completion of the reaction, the reaction product liquid was subjected to centrifugal separation to obtain about 500 ml of supernatant liquid, which did not contain phenols such as phenol, catechol, resorcinol, etc. even in a trace amount except hydroquinone. To this supernatant liquid was added methyl isobutyl ketone at a volume ratio of 1.0 of the former to 0.5 of the latter and extraction and transfer of hydroquinone were repeated twice. The obtained about 500 ml of methyl isobutyl ketone solution was evaporated to dryness in a rotary evaporater to obtain 260 mg of pinkish hydroquinone having purity of 995. The yield was about 74% which was high.

EXAMPLE 5

In the same manner as in Example 4, *Mycobacterium vaccae* ATCC 29678 was cultured using n-butane as a carbon source at 30° C. for 72 hours. The obtained cells were suspended in a phosphate buffer solution (pH 7.0) containing $Mg^{++}$, followed by adding thereto phenol in an amount of 500 mg/liter. Reaction was carried out at 32° C. with shaking to promote dissolution of oxygen. When glucose was added to the reaction liquid in an amount of 1000 mg/liter at the time of reaction, the hydroquinone producing rate was as high as 2 times the rate when no glucose was added.

EXAMPLE 6

*Mycobacterium vaccae* ATCC 29678 was cultured in a complete synthetic culture medium (pH 7.0) using propane as a carbon source at 30° C. for 72 hours. The propane as a carbon source was supplied to a space in the reactor as a mixed gas with air (propane:air=1:3). After culturing, the cells obtained by centrifugal separation was suspended in a complete synthetic culture medium (pH 7.0) containing no carbon source to obtain suspension in which concentration of cells was 2.0 mg/ml. To 20 ml of this suspension was added phenol in an amount of 500 mg/liter and reaction was effected at 30° C. for 24 hours with shaking. As a result, 255 mg/liter of hydroquinone was produced in supernatant liquid. No by-products were detected.

EXAMPLE 7

*Mycobacterium vaccae* ATCC 29678 was cultured in a complete synthetic culture medium (pH 7.0) containing glucose (1 weight % added) as a carbon source at 30° C. for 48 hours. Cells obtained were suspended in a phosphate buffer solution (pH 7.0) containing Mg++ to obtain suspension in which concentration of cells was 10 mg/ml. To 20 ml of this suspension was added phenol in an amount of 500 mg/liter and reaction was carried out at 30° C. for 24 hours with shaking. As a result, 475 mg/liter of hydroquinone was produced in supernatant liquid. No unaltered phenol remained and no by-products were detected.

EXAMPLE 8

*Mycobacterium vaccae* ATCC 29678 was cultured in a complete synthetic culture medium (pH 7.2) containing n-butanol (0.5 weight % added) as a carbon source at 30° C. for 48 hours. Cells obtained were suspended in a phosphate buffer solution (pH 7.0) containing Mg++ to obtain suspension in which concentration of cells was 10 mg/ml. To 20 ml of this suspension was added phenol in an amount of 500 mg/liter and reaction was effected at 28° C. for 24 hours with shaking. As a result, 300 mg/liter of hydroquinone was produced in supernatant liquid. No by-products were detected.

EXAMPLE 9

In the same manner as in Example 4, *Mycobacterium album* ATCC 29676 was cultured containing n-butane as a carbon source at 30° C. for 72 hours. Cells obtained were suspended in a phosphate buffer solution (pH 7.0) containing Mg++ to obtain suspension in which concentration of cells was 10 mg/ml. To 20 ml of this suspension was added phenol in an amount of 500 mg/liter and reaction was carried out at 30° C. for 24 hours with shaking. As a result, 200 mg/liter of hydroquinone was produced in supernatant liquid. No by-products were detected.

EXAMPLE 10

In the same manner as in Example 4, *Mycobacterium album* ATCC 29676 was cultured at 30° C. for 70 hours. Cells obtained were suspended in a phosphate buffer solution (pH 7.0) containing Mg++ to obtain suspension in which concentration of cells was 15 mg/ml. To 20 ml of this suspension were added 11 μl of benzene and 0.5 ml of an aqueous glucose solution (4%) and reaction was effected at 30° C. for 20 hours. As a result, 250 mg/liter of hydroquinone was produced in supernatant liquid. Phenol, catechol and resorcinol were not present in the supernatant liquid.

Composition of the complete synthetic culture medium (excluding carbon source) used in these Examples is as follows:

| | | |
|---|---|---|
| Ammonium sulfate (NH$_4$)$_2$SO$_4$ | 3.0 | g |
| Potassium dihydrogenphosphate KH$_2$PO$_4$ | 1.4 | g |
| Magnesium sulfate MgSO$_4$.7H$_2$O | 0.2 | g |
| Disodium hydrogenphosphate Na$_2$HPO$_4$ | 2.1 | g |
| Trace amount of mineral mixed liquid | 2 | ml |
| Distilled water | 1 | liter |
| pH | 7.0 | |
| Composition of trace amount of mineral mixed liquid | | |
| Ferric citrate.XH$_2$O | 6.0 | g |
| CaCl$_2$.2H$_2$O | 4.0 | g |
| ZnSO$_4$.7H$_2$O | 2.0 | g |
| MnCl$_2$.4H$_2$O | 1.0 | g |
| CuSO$_4$.5H$_2$O | 0.01 | g |
| KI | 0.1 | g |
| (NH$_4$)$_6$Mo$_7$O$_{24}$.4H$_2$O | 0.1 | g |
| CoCl$_2$.6H$_2$O | 0.1 | g |
| H$_3$BO$_3$ | 0.2 | g |
| NaCl | 5.0 | g |
| Distilled water | 1 | liter |

We claim:

1. A process for producing hydroquinone which comprises the following steps:
   (a) contacting bacterial cells or enzyme obtained by crushing the cells thereof in an aqueous medium with benzene or phenol under reaction conditions of a temperature from 25 to 35 degrees Celsius and a pH about 7, wherein said cells are obtained by culturing microorganism selected from the group consisting of *Mycobacterium album* and *Mycobacterium vaccae* in a culture medium and wherein said cells are capable of oxidizing benzene or phenol;
   (b) providing to said aqueous medium a molecular oxygen-containing gas; and
   (c) recovering hydroquinone from a reaction product solution.

2. A process according to claim 1 wherein the *Mycobacterium album* is *Mycobacterium album* ATCC 29676.

3. A process according to claim 1 wherein the *Mycobacterium vaccae* is *Mycobacterium vaccae* ATCC 29678.

* * * * *